(12) United States Patent
Zhang et al.

(10) Patent No.: US 9,238,842 B2
(45) Date of Patent: Jan. 19, 2016

(54) **METHOD FOR DETECTING THE GENUS OF *BACILLUS* IN SAMPLES FROM OIL RESERVOIRS**

(71) Applicant: China University of Geosciences, Beijing, Beijing (CN)

(72) Inventors: Fan Zhang, Beijing (CN); Yuehui She, Jingzhou (CN); Dujie Hou, Beijing (CN); Lujun Chai, Beijing (CN)

(73) Assignee: China University of Geosciences, Beijing, Beijing (CN)

( * ) Notice: Subject to any disclaimer, the term of this patent is extended or adjusted under 35 U.S.C. 154(b) by 199 days.

(21) Appl. No.: 13/868,561

(22) Filed: Apr. 23, 2013

(65) Prior Publication Data

US 2014/0155273 A1    Jun. 5, 2014

(30) Foreign Application Priority Data

Nov. 30, 2012   (CN) .......................... 2012 1 0499739

(51) Int. Cl.
*C12Q 1/68*    (2006.01)
(52) U.S. Cl.
CPC ..................................... *C12Q 1/689* (2013.01)
(58) Field of Classification Search
None
See application file for complete search history.

(56) References Cited

U.S. PATENT DOCUMENTS 4,799,545 A * 1/1989 Silver et al. .................. 166/246

OTHER PUBLICATIONS

Da Cunha et al., Oil biodegradation by Bacillus strains isolated from the rock of an oil reservoir located in a deep-water production basin in Brazil, 2006, Applied Microbiology and Biotechnology 73(4): 949-959.*
Rosnes et al., Ch. R-17 Degradation of Glucose and Production of H2S by a Consortium of Thermophilic Bacteria Under Simulated Reservoir Conditions, 1991, Developments in Petroleum Science 31: 265-276.*
Faris et al., Spectrally resolved absolute fluorescence cross sections for bacillus spores, 1997, Applied Optics 36(4): 958-967.*
Amann et al., Phylogenetic Identification and in Situ Detection of Individual Microbial Cells without Cultivation, Microbiological Reviews, Mar. 1995, p. 143-169, vol. 59, No. 1.
Head et al., Microbial Evolution, Diversity, and Ecology: A Decade of Ribosomal RNA Analysis of Uncultivated Microorganisms, Microbial Ecology, 1998, p. 1-21, vol. 35.

* cited by examiner

*Primary Examiner* — Robert Yamasaki
(74) *Attorney, Agent, or Firm* — The Webb Law Firm

(57) ABSTRACT

The invention provides a quick method for detecting the genus of *Bacillus* in samples from oil reservoirs, which comprise: collecting samples from oil reservoirs; inactivating microbes except for spore-forming *Bacillus* in the samples through high temperature; collecting spores from the samples; incubating the collected spores in a medium, and stimulating to resurrect *Bacillus* under in situ temperatures of the oil reservoirs; detecting the resurrected *Bacillus* in the cultures using molecular biological techniques. The present invention provides an effective method to detect the genus of *Bacillus* in samples from oil reservoirs, which is conducive to the discovery of the functional *Bacillus* for microbial enhanced oil recovery (MEOR) and to revealing the ecosystem of *Bacillus* in oil reservoirs.

6 Claims, 1 Drawing Sheet

METHOD FOR DETECTING THE GENUS OF *BACILLUS* IN SAMPLES FROM OIL RESERVOIRS

TECHNICAL FIELD

The present invention relates to a quick method for detecting *Bacillus* in samples from oil reservoirs. More specifically, the present invention relates to a method to reveal the diversity of *Bacillus* in oil reservoirs, by the combination of culture-dependent microbiological techniques and culture-independent molecular biological techniques.

BACKGROUND ART

With the detection and isolation of microbes in samples from oil reservoirs, researchers found out that not all microbes in oil reservoirs are harmful to oil exploitation, the metabolism products and activity of some microbes in oil reservoirs can be use to enhance oil recovery. Therefore, microbial enhanced oil recovery (MEOR) was proposed and implemented as one of tertiary measures to enhance oil recovery.

The principal part of MEOR is potential microbes. According to studies of functional microbes for MEOR, strains of *Bacillus* are documented as a functional group of microbes for MEOR. *Bacillus* is able to produce biosurfactant that can lower interfacial tension between crude oil and aqueous liquid and rocks, so as to improve the mobility of the crude oil and significantly increase the production of the oil; *Bacillus* can increase the production of the oil by degrading long chain hydrocarbons to decrease viscosity of crude oil and to improve the mobility of crude oil; *Bacillus* can also increase the production of the oil by producing polymer to selectively plug in oil reservoirs, so as to promote the volumetric sweep efficiency of injected water.

For studies and field trials of MEOR, investigating microbes inhabiting in oil reservoirs is a key and primary step to discover potential microbes and design strategies of field trials.

Traditional culture-dependent microbial methods are applied by researchers to isolate microbes from oil reservoirs and identify their potential functions to MEOR. However, the procedures to enrich and isolate microbes are complex, in most of cases, special media, special carbon resources and tens of incubations cycle during procedure of enrichment were needed. In addition, only a small percentage (less than 1%) (Amann et al., 1995) of viable microbes can be cultured on known nutrient media using the culture-dependent traditional techniques. Bacteria detected by traditional microbial methods are a minor part of the microbes inhabiting in oil reservoirs.

Recently, molecular microbial ecology represents a development in research methods, which contains utilizing techniques of molecular biology to investigate the ecology of microbes and offers new techniques to facilitate the detection of microbes. Researchers have investigated microbial diversity in samples collected from various oil reservoirs using culture-independent molecular biological methods.

Multiple groups of microorganisms with diverse phylogenetic affiliations have routinely been detected from oil reservoirs. However, an obscuring result from the studies based on culture-independent molecular techniques was that, in most of clone libraries, few to no clones or sequences detected were affiliated with the genus of *Bacillus*. These results insert an impression to us that *Bacillus* is rare or absent in these oil reservoirs.

When investigating microbial diversity in the original samples from oil reservoirs based on culture-independent molecular biological methods, DNA extraction from the spore-forming bacteria is more difficult than from other microbes, in addition, molecular biological methods is unable to detect a small proportion of 0.1-1% of bacteria (Head et al., 1998), both of which might be the major reasons for neglection of the group of *Bacillus* in clone libraries of samples from oil reservoirs.

The *Bacillus* is a group of Gram-positive, spore-forming bacteria, which is a potential microbial group for MEOR. How to detect and enrich the genus of *Bacillus* in samples from oil reservoirs is an urgent question faced by us. Considering the disadvantages and advantages of culture-dependent and culture-independent microbial methods and molecular biological methods, we provide a method to quickly detect the genus inhabiting in samples collected from oil reservoirs. This method is a combination of the advantages of both culture-dependent and culture-independent microbial methods and molecular biological methods.

CONTENTS OF THE INVENTION

It is an object of present invention to provide a method for detecting the genus of *Bacillus* in samples from oil reservoirs based on the advantages of both culture-dependent and culture-independent microbial methods and molecular biological methods, which provides an effective method to discover the functional *Bacillus* for microbial enhanced oil recovery (MEOR) and reveal the ecosystem of *Bacillus* in oil reservoirs.

According to one aspect, the present invention relates to a method for enriching and detecting *Bacillus* in samples from oil reservoirs based on culture-dependent coupled with culture-independent molecular biological techniques, which comprise:

(1) collecting samples from oil reservoirs;
(2) inactivating microbes except for spore-forming *Bacillus* in the samples through high temperature;
(3) collecting spores from the samples;
(4) incubating the collected spores in an appropriate medium, and stimulating to resurrect the *Bacillus* under the in situ temperatures of the oil reservoirs;
(5) detecting the resurrected *Bacillus* in the cultures using molecular biological techniques.

Wherein, said reservoirs are various oil reservoirs with different geological conditions and exploitation methods.

Wherein said samples include oil-water samples collected directly from the wellheads of injection wells, production wells, formation water samples, flowing-back sample of the oil wells, core samples from oil reservoirs.

wherein, the step of collection samples comprising: an oil-water sample are collected and put into a sterile plastic bottle, full filled and sealed and recorded the in situ temperature of the oil reservoir.

wherein, the step of inactivating microbes except for spore-forming *Bacillus* in the samples through high temperature is as follow: a 500 ml of the oil-water sample is transferred into a 2 L sterile flask in a sterile condition, and sealed with a sterile ventilate membrane. Put the flask on an electric heater and keep the oil-water sample inside boiling for 10 minutes, cool down at room temperature.

The step of collecting spores from the samples treated in step 2 is that after cool down, the oil-water sample is transferred into 50 ml sterile centrifuge tubes in sterile condition and centrifuged at 10,000×g for 15 minutes, remove the supernatant to a sterile flask for medium preparation;

Then, resuspend the pellets of precipitation in each centrifuge tube with 1 ml sterile water, and combine the suspension from the centrifuge tubes into a 10 ml mixture; the mixture contains spores.

The next step consists in the incubation and cultivation for resurrection. The 10 ml mixture collected in the first step is incubated into a 100 ml flask with 30 ml sterilized appropriate medium, seal the cover of the flask, cultivate to resurrect the *Bacillus* at in situ temperature of the oil reservoir from which the sample was collected for 7-15 days to obtain the resurrection medium.

In the step of cultivation, the optimal temperature is the in situ temperature of the oil reservoir from which the sample was collected. Different oil reservoirs have different in situ temperatures, and the range of the in situ temperature of the oil reservoirs is 10° C.-110° C.

In the step of incubation and cultivation for resurrection, an appropriate medium is needed. As used herein, an "appropriate medium" is intended to mean a medium compatible with the environment from with the sample was collected and can provide nutrients for spores stimulation. In the invention for oil-water samples from oil reservoirs, the supernatant collected in the step (3) can be the appropriate water containing suitable ingredients for medium preparation. The medium (100 ml) includes the supernatant collected in the step (3), 2 g molasses, 0.16 g (NH4)2HPO4, 0.2 g KNO3 and 2 g crude oil, autoclave at 121° C. for 20 minutes. The crude oil is oil from the oil reservoirs where the sample was collected.

The step of detecting microbes in the culture can based on molecular biological techniques is as follow: a 5 ml of the culture is transferred into a sterile centrifuge tube in sterile condition, and centrifuge at 10,000×g for 10 minutes for cell collection, remove the supernatant and add 1 ml distilled water to resuspend the cells sedimentation. DNA in the resuspension were extracted following the manufacturer's protocol of the FastDNA Spin Kit for Soil, and extracted DNA were amplified by PCR using specific 16S RNA gene primers for bacteria to construct clone library, the representative clones are sequenced and are analysed to determine their phylogenetic affiliations.

Most strains of *Bacillus* in samples from oil reservoirs might have been overlooked as their character of spore-forming and the disadvantages of detecting methods. The present invention relates to a quick method to detect and enrich *Bacillus* from samples collected from oil reservoirs based on culture-dependent methods coupled with culture-independent methods, which provide an effective method to discover the functional *Bacillus* and to reveal the ecosystem of *Bacillus* in oil reservoirs.

DESCRIPTION OF FIGURES

FIG. 1 is a photo of a collected spore by the method of the invention pictured by transmission electron microscope.

MODE OF CARRYING OUT THE INVENTION

Different oil reservoirs have different in situ temperatures. Eight samples from four water-flooded oil reservoirs with different in situ temperatures (two samples respectively are from an injection well and a production well of each water-flooded oil reservoir), and two samples from a polymer-flooded oil reservoir were used in the invention.

The investigations of microbial diversity in the five oil reservoirs reported that few to no sequence of *Bacillus* were detected. Results obtained in these examples determine effectiveness, extensity and feasibility of the invention.

Example 1

Detection of *Bacillus* in the Samples from the Oil Reservoir with Low In Situ Temperature Two samples were collected from the No. 6 oil reservoir with an in situ temperature of 25° C. in Xinjiang oil field (China). One sample was collected from the injection well of T6186 and the other was collected from the production well of T6073. The primary investigation of microbial diversity was reported that few to no sequences were affiliated with *Bacillus* in the both clone libraries constructed from the two original samples.

According to the methods of the invention, the steps of detecting the genus of *Bacillus* are as follows:

1. Collecting samples from the oil reservoir of No. 6. Oil-water samples were collected directly from the wellheads of the injection well of T6186 and the production well of T6073, and put into two sterile plastic bottles, full filled and sealed, and recorded the in situ temperature of the oil reservoir of 25° C. after which, the experiments were carried out ASAP.

2. Inactivating microbes except for spore-forming *Bacillus* in the samples through high temperature. A 500 ml of each the oil-water sample was transferred into a 2 L sterile flask in a sterile condition, and sealed with a sterile ventilate membrane. Put the flask on an electric heater with asestos net and keep the oil-water sample inside boiling for 10 minutes, cool down at room temperature.

3. Collecting spores from the samples. After cool down, the oil-water sample treated in step 2 was transferred into 50 ml sterile centrifuge tubes in a sterile condition, and centrifuged at 10,000×g for 15 minutes, remove the supernatant to a sterile flask for medium preparation;

resuspend the pellets of precipitation in each centrifuge tube with 1 ml sterile water, and combine the suspension from the centrifuge tubes into a 10 ml mixture; the mixture contains spores.

FIG. 1 is a photo of a collected spore by the method of the invention pictured by transmission electron microscope.

4. Incubating the collected spores in an appropriate medium, and stimulating to resurrect the *Bacillus* under the in situ temperatures of the oil reservoirs: The 10 ml mixture collected in step 3 was incubated into a 100 ml flask with 30 ml sterilized appropriate medium, sealed the cover of the flask, cultivated to resurrect the *Bacillus* at the in situ temperature of 25° C. of the oil reservoir for 7 days at 150 rmp to obtain the resurrection medium.

Said medium is a medium compatible with the environment from with the sample was collected and can provide nutrients for spores stimulation. The medium (100 ml) includes the supernatant collected in step 3, 2 g molasses, 0.16 g (NH4)2HPO4, 0.2 g KNO3 and 2 g crude oil, autoclave at 121° C. for 20 minutes. The crude oil is oil from the oil reservoir of No. 6.

5. Detecting the *Bacillus* in the cultures using molecular biological techniques. A 5 ml of the culture obtained in step 4 was transferred into a sterile centrifuge tube in a sterile condition, and centrifuged at 10,000×g for 10 minutes for cell collection, removed the supernatant and added 1 ml distilled water to resuspend the cells sedimentation. DNA in the resuspension were extracted following the manufacturer's protocol of the FastDNA Spin Kit for Soil, the extracted DNA were amplified by PCR using specific 16S RNA gene primers for bacteria to construct clone library, the representative clones were sequenced and were analysed to determine their phylogenetic affiliations.

Two 16S rRNA gene clone libraries (N6PB and N6IB) were constructed from the two cultures cultivated following the invention. 5 and 6 OTUs were identified in clone libraries of N6PB and N6IB, respectively. 98.8% of the sequences in clone library of N6PB were identified as *Bacillus*, dominated by *Bacillus* sp. (Table 1). In clone library of N6IB, 95.4% of sequences were also affiliated with *Bacillus*, dominated by *Bacillus flexus* (Table 2).

TABLE 1

Microbes of *Bacillus* detected in the sample of T6073 by the method of the invention

| OTU | Clone abundance (%) | The most relative sequences in GenBank | similarity (%) |
|---|---|---|---|
| N6PB-1 | 90.7 | *Bacillus* sp. JQ814756 | 99 |
| N6PB-2 | 5.7 | *Bacillus* sp. JQ814756 | 100 |
| N6PB-3 | 1.2 | *Bacillus* sp. JQ814756 | 96 |
| N6PB-4 | 1.2 | *Bacillus* flexus JN315892 | 100 |
| N6PB-5 | 1.2 | Uncultured Bacterium JN882107 | 100 |

TABLE 2

Microbes of *Bacillus* detected in the sample of T6186 by the method of the invention

| OTU | Clone abundance (%) | The most relative sequences in GenBank | similarity (%) |
|---|---|---|---|
| N6IB-1 | 78.4 | *Bacillus* flexus JN315892 | 99 |
| N6IB-2 | 13.6 | *Bacillus* flexus JN315892 | 100 |
| N6IB-3 | 2.3 | *Bacillus* sp. JQ726697 | 100 |
| N6IB-4 | 1.1 | *Bacillus* flexus JN315892 | 96 |
| N6IB-5 | 2.3 | Uncultured bacterium JN882107 | 94 |
| N6IB-6 | 2.3 | Uncultured bacterium JF926709 | 100 |

Example 2

Detection of the *Bacillus* in the Samples from the Oil Reservoir with Mesothermal In Situ Temperature Two samples were collected from the Yan 9 oil reservoir with a mesothermal in situ temperature of 40° C. in Changing oil field (China). One sample was collected from the injection well of L28-45 and the other was collected from the production well of L28-46. The primary investigation of microbial diversity in the two samples was reported that few to no sequences were affiliated with *Bacillus* in the both clone libraries constructed from the two original samples.

According to the methods of the invention, the steps of detecting the genus of *Bacillus* are as follows:
1. Collecting samples from the oil reservoir of Yan 9. Oil-water samples were collected directly from the injection well of L28-45 and the production well of L28-46, and put into two sterile plastic bottles, full filled and sealed, in addition, recorded the in situ temperature of the oil reservoir of 40° C., after which, the experiments were carried out ASAP.
2. Inactivating microbes except for spore-forming *Bacillus* in the samples through high temperature. A 500 ml of each the oil-water sample was transferred into a 2 L sterile flask in a sterile condition, and sealed with a sterile ventilate membrane. Put the flask on an electric heater with asestos net and keep the oil-water sample inside boiling for 10 minutes, cool down at room temperature.
3. Collecting spores from the samples. After cool down, the oil-water sample treated in step 2 was transferred into 50 ml sterile centrifuge tubes in a sterile condition, and centrifuged at 10,000×g for 15 minutes, remove the supernatant to a sterile flask for medium preparation; resuspend the pellets of precipitation in each centrifuge tube with 1 ml sterile water, and combine the suspension from the centrifuge tubes into a 10 ml mixture; the mixture contains spores.
4. Incubating the collected spores in an appropriate medium, and stimulating to resurrect the *Bacillus* under the in situ temperatures of the oil reservoirs. The 10 ml mixture collected in step 3 was incubated into a 100 ml flask with 30 ml sterilized appropriate medium, sealed the cover of the flask, cultivated to resurrect the *Bacillus* at the in situ temperature of 40° C. of the oil reservoir for 9 days at 150 rmp to obtain the resurrection medium.

Said medium is a medium compatible with the environment from with the sample was collected and can provide nutrients for spores stimulation. The medium (100 ml) includes the supernatant collected in step 3, 2 g molasses, 0.16 g (NH4)2HPO4, 0.2 g KNO3 and 2 g crude oil, autoclave at 121° C. for 20 minutes. The crude oil is oil from the oil reservoir of Yan 9.

5. Detecting the *Bacillus* in the cultures using molecular biological techniques. A 5 ml of the culture obtained in step 4 was transferred into a sterile centrifuge tube in a sterile condition, and centrifuged at 10,000×g for 10 minutes for cell collection, removed the supernatant and added 1 ml distilled water to resuspend the cells sedimentation. DNA in the resuspension were extracted following the manufacturer's protocol of the FastDNA Spin Kit for Soil, and the extracted DNA were amplified by PCR using specific 16S RNA gene primers for bacteria to construct clone library, the representative clones were sequenced and were analysed to determine their phylogenetic affiliations.

Two 16S rRNA gene clone libraries (Y9PB and Y9IB) were constructed from the two samples. 4 and 4 OTUs were identified in in Y9PB and Y9IB, respectively. 100% of the sequences in clone library of Y9PB were identified as *Bacillus*, dominated by *Brevibacillus agri*. (Table 3). In clone library of Y9IB, 100% of sequences were also affiliated with *Bacillus*, dominated by *Paenibacillus* sp. (Table 4).

TABLE 3

Microbes of *Bacillus* detected in the sample of L28-46 by the method of the invention

| OTU | Clone abundance (%) | The most relative sequences in GenBank | similarity (%) |
|---|---|---|---|
| Y9PB-1 | 91.9 | *Brevibacillus agri* NR_040983 | 99 |
| Y9PB-2 | 4.8 | *Brevibacillus agri* NR_040983 | 99 |
| Y9PB-3 | 2.2 | *Bacillus* sp. HM099654 | 95 |
| Y9PB-4 | 1.1 | *Bacillus oceanisediminis* JF411234 | 97 |

TABLE 4

Microbes of *Bacillus* detected in the sample of L28-45 by the method of the invention

| OTU | Clone abundance (%) | The most relative sequences in GenBank | similarity (%) |
|---|---|---|---|
| Y9IB-1 | 93.3 | *Paenibacillus* sp. AY382189 | 99 |
| Y9IB-1 | 3.4 | *Paenibacillus* sp. AY382189 | 100 |

TABLE 4-continued

Microbes of *Bacillus* detected in the sample of L28-45 by the method of the invention

| OTU | Clone abundance (%) | The most relative sequences in GenBank | similarity (%) |
|---|---|---|---|
| Y9IB-3 | 2.2 | *Brevibacillus agri* NR_040983 | 100 |
| Y9IB-4 | 1.1 | *Bacillus* sp. HM099654 | 98 |

Example 3

Detection of the *Bacillus* in the Samples from the Oil Reservoir with High In Situ Temperature Two samples were collected from the J68 oil reservoir with a high in situ temperature of 60° C. in Liaohe oil field (China). One sample was collected from the injection well of J68-50 and the other was collected from the production well of J68-51C. The primary investigation of microbial diversity in the two samples was reported that few to no sequences were affiliated with *Bacillus* in the both clone libraries constructed from the two original samples.

1. Collecting samples from the oil reservoir of J68. Oil-water samples were collected directly from the wellheads of the injection well of J68-50 and the production well of J68-51C, and put into two sterile plastic bottles, full filled and sealed, in addition, recorded the in situ temperature of the oil reservoir of 60° C., after which, the experiments were carried out ASAP.
2. Inactivating microbes except for spore-forming *Bacillus* in the samples through high temperature. A 500 ml of each the oil-water sample was transferred into a 2 L sterile flask in a sterile condition, and sealed with a sterile ventilate membrane. Put the flask on an electric heater with asestos net and keep the oil-water sample inside boiling for 10 minutes, cool down at room temperature.
3. Collecting spores from the samples. After cool down, the oil-water sample treated in step 2 was transferred into 50 ml sterile centrifuge tubes and centrifuged at 10,000×g for 15 minutes, remove the supernatant to a sterile flask for medium preparation;
resuspend the pellets of precipitation in each centrifuge tube with 1 ml sterile water, and combine the suspension from the centrifuge tubes into a 10 ml mixture; the mixture contains spores.
4. Incubating the collected spores in an appropriate medium, and stimulating to resurrect the *Bacillus* under the in situ temperatures of the oil reservoirs. The 10 ml mixture collected in step 3 was incubated into a 100 ml flask with 30 ml sterilized appropriate medium, sealed the cover of the flask, cultivated to resurrect the *Bacillus* at the in situ temperature of 60° C. of the oil reservoir for 10 days at 150 rmp to obtain the resurrection medium.
Said medium is a medium compatible with the environment from with the sample was collected and can provide nutrients for spores stimulation. The medium (100 ml) includes the supernatant collected in step 3, 2 g molasses, 0.16 g (NH4)2HPO4, 0.2 g KNO3 and 2 g crude oil, autoclave at 121° C. for 20 minutes. The crude oil is oil from the oil reservoir of J68.
5. Detecting the *Bacillus* in the cultures using molecular biological techniques. A 5 ml of the culture obtained in step 4 was transferred into a sterile centrifuge tube in a sterile condition, and centrifuged at 10,000×g for 10 minutes for cell collection, removed the supernatant and added 1 ml distilled water to resuspend the cells sedimentation. DNA in the resuspension were extracted following the manufacturer's protocol for the FastDNA Spin Kit for Soil, and the extracted DNA were amplified by PCR using specific 16S RNA gene primers for bacteria to construct clone library, the representative clones were sequenced and were analysed to determine their phylogenetic affiliations.

Two 16S rRNA gene clone libraries (J68PB and J68IB) were constructed from the two samples following the invention. 7 and 5 OTUs were identified in clone libraries of J68PB and J68IB, respectively. 95.6% of the sequences in clone library of J68PB were identified as *Bacillus*, dominated by *Geobacillus thermodenitrificans* (Table 5). In clone library of J68IB, 100% of sequences were also affiliated with *Bacillus*, dominated by *Bacillus thermoamylovorans* and *Bacillus cereus* (Table 6).

TABLE 5

Microbes of *Bacillus* detected in the sample of J68-51C by the method of the invention

| OTU | Clone abundance (%) | The most relative sequences in GenBank | similarity (%) |
|---|---|---|---|
| J68PB-1 | 75.6 | *Geobacillus thermodenitrificans* NR_043021 | 99 |
| J68PB-2 | 14.4 | *Geobacillus thermodenitrificans* FJ823098 | 99 |
| J68PB-3 | 2.2 | *Geobacillus thermodenitrificans* GU903484 | 99 |
| J68PB-4 | 1.1 | *Geobacillus thermodenitrificans* NR_043021 | 99 |
| J68PB-5 | 1.1 | *Geobacillus thermodenitrificans* FJ491391 | 99 |
| J68PB-6 | 1.1 | *Geobacillus thermodenitrificans* FJ491391 | 99 |
| J68PB-7 | 4.4 | Uncultured bacterium DQ675030 | 99 |

TABLE 6

Microbes of *Bacillus* detected in the sample of J68-50 by the method of the invention

| OTU | Clone abundance (%) | The most relative sequences in GenBank | similarity (%) |
|---|---|---|---|
| J68IB-1 | 87.8 | *Bacillus thermoamylovorans* HM030742 | 100 |
| J68IB-2 | 6.7 | *Bacillus cereus* EE428235 | 99 |
| J68IB-3 | 3.3 | *Bacillus* sp.AB375736 | 99 |
| J68IB-4 | 1.1 | *Geobacillus thermodenitrificans* FJ491391 | 100 |
| J68IB-5 | 1.1 | *Bacillus cereus*. EE428235 | 98 |

Example 4

Detection of the *Bacillus* in the Samples from the Oil Reservoir with Super High In Situ Temperature Two samples were collected from the V 4 oil reservoir with a super high in situ temperature of 70° C. in Henan oil field (China). One sample was collected from the injection well of V187 and the other was collected from the production well of V149. The primary investigation of microbial diversity in the two samples was reported that few to no sequences were affiliated with *Bacillus* in the both clone libraries constructed from the two original samples.

1. Collecting samples from the oil reservoir of V 4. Oil-water samples were collected directly from the injection well of V187 and the production well of V149, and put into two sterile plastic bottles, full filled and sealed, in addition, recorded the in situ temperature of the oil reservoir of 70° C., after which, the experiments were carried out ASAP.

2. Inactivating microbes except for spore-forming *Bacillus* in the samples through high temperature. A 500 ml of each the oil-water sample was transferred into a 2 L sterile flask in a sterile condition, and sealed with a sterile ventilate membrane. Put the flask on an electric heater with asestos net and keep the oil-water sample inside boiling for 10 minutes, cool down at room temperature.

3. Collecting spores from the samples. After cool down, the oil-water sample treated in step 2 was transferred into 50 ml sterile centrifuge tubes in a sterile condition, and centrifuged at 10,000×g for 15 minutes, remove the supernatant to a sterile flask for medium preparation;

resuspend the pellets of precipitation in each centrifuge tube with 1 ml sterile water, and combine the suspension from the centrifuge tubes into a 10 ml mixture; the mixture contains spores.

4. Incubating the collected spores in an appropriate medium, and stimulating to resurrect the *Bacillus* under the in situ temperatures of the oil reservoirs. The 10 ml mixture collected in step 3 was incubated into a 100 ml flask with 30 ml sterilized appropriate medium, sealed the cover of the flask, cultivated to resurrect the *Bacillus* at the in situ temperature of 70° C. of the oil reservoir for 12 days at 150 rmp to obtain the resurrection medium.

Said medium is a medium compatible with the environment from with the sample was collected and can provide nutrients for spores stimulation. The medium (100 ml) includes the supernatant collected in step 3, 2 g molasses, 0.16 g (NH4)2HPO4, 0.2 g KNO3 and 2 g crude oil, autoclave at 121° C. for 20 minutes. The crude oil is oil from the oil reservoir of V4.

5. Detecting the *Bacillus* in the cultures using molecular biological techniques. A 5 ml of the culture obtained in step 4 was transferred into a sterile centrifuge tube in a sterile condition, and centrifuged at 10,000×g for 10 minutes for cell collection, removed the supernatant and added 1 ml distilled water to resuspend the cells sedimentation. DNA in the resuspension were extracted following the manufacturer's protocol of the FastDNA Spin Kit for Soil, and the extracted DNA were amplified by PCR using specific 16S RNA gene primers for bacteria to construct clone library, the representative clones were sequenced and were analysed to determine their phylogenetic affiliations.

Two 16S rRNA gene clone libraries (V4PB and V4IB) were constructed from the two cultures cultivated following the invention. 5 and 5 OTUs were identified in V4PB and V4IB, respectively. 100% of the sequences in clone library of V4PB were identified as *Bacillus*, dominated by *Bacillus* sp., and included a small percentage of *Aneurinibacillus aneurinilyticus* (Table 7); In clone library of V4IB, 100% of sequences were also affiliated with *Bacillus*, dominated by *Bacillus pseudofirmus*, and *Aneurinibacillus migulanus* occupied a percentage of 14.6% (Table 8).

TABLE 7

Microbes of *Bacillus* detected in the sample of V149 by the method of the invention

| OTU | Clone abundance (%) | The most relative sequences in GenBank | similarity (%) |
|---|---|---|---|
| V4PB-1 | 71 | *Bacillus* sp. EU520305 | 100 |
| V4PB-2 | 14.5 | *Bacillus* sp. AY556413 | 99 |

TABLE 7-continued

Microbes of *Bacillus* detected in the sample of V149 by the method of the invention

| OTU | Clone abundance (%) | The most relative sequences in GenBank | similarity (%) |
|---|---|---|---|
| V4PB-3 | 10.8 | *Bacillus* sp. EU520305 | 99 |
| V4PB-4 | 2.4 | *Aneurinibacillus aneurinilyticus* GU549488 | 99 |
| V4PB-5 | 1.2 | *Bacillus pseudofirmus* AF406790 | 99 |

TABLE 8

Microbes of *Bacillus* detected in the sample of V187 by the method of the invention

| OTU | Clone abundance (%) | The most relative sequences in GenBank | similarity (%) |
|---|---|---|---|
| V4IB-1 | 80.9 | *Bacillus pseudofirmus* AF406790 | 100 |
| V4IB-2 | 14.6 | *Aneurinibacillus migulanus* DQ350838 | 99 |
| V4IB-3 | 2.2 | *Bacillus* sp. EU520305 | 99 |
| V4IB-4 | 1.1 | *Bacillus* sp. EU520305 | 100 |
| V4IB-5 | 1.1 | *Bacillus pseudofirmus* AF406790 | 99 |

Example 5

Detection of the *Bacillus* in the Samples from the Polymer-Flooded Oil Reservoir Two samples were collected from the N 2 oil reservoir, which is a polymer-flooded oil reservoir with an in situ temperature of 40° C. One sample was collected from the injection well of N2-1 and the other was collected from the production well of N2-2. The primary investigation of microbial diversity in the two samples was reported that no sequences were affiliated with *Bacillus* in the both clone libraries constructed from the two original samples.

1. Collecting samples from the oil reservoir of N 2. Oil-water samples were collected directly from the injection well of N2-1 and the production well of N2-2, and put into two sterile plastic bottles, full filled and sealed, in addition, recorded the in situ temperature of the oil reservoir, after which, the experiments were carried out ASAP.

2. Inactivating microbes except for spore-forming *Bacillus* in the samples through high temperature. A 500 ml of each the oil-water sample was transferred into a 2 L sterile flask in a sterile condition, and sealed with a sterile ventilate membrane. Put the flask on an electric heater with asestos net and keep the oil-water sample inside boiling for 10 minutes, cool down at room temperature.

3. Collecting spores from the samples. After cool down, the oil-water sample treated in step 2 was transferred into 50 ml sterile centrifuge tubes in a sterile condition and centrifuged at 10,000×g for 15 minutes, remove the supernatant to a sterile flask for medium preparation;

resuspend the pellets of precipitation in each centrifuge tube with 1 ml sterile water, and combine the suspension from the centrifuge tubes into a 10 ml mixture; the mixture contains spores.

4. Incubating the collected spores in an appropriate medium, and stimulating to resurrect the *Bacillus* under the in situ temperatures of the oil reservoirs. The 10 ml mixture collected in step 3 was incubated into a 100 ml flask with 30 ml sterilized appropriate medium, sealed the cover of the flask, cultivated to resurrect the *Bacillus* at the in situ temperature of the oil reservoir for 15 days at 150 rmp to obtain the resurrection medium.

Said medium is a medium compatible with the environment from with the sample was collected and can provide nutrients for spores stimulation. The medium (100 ml) includes the supernatant collected in step 3, 2 g molasses, 0.16 g (NH4)2HPO4, 0.2 g KNO3 and 2 g crude oil, autoclave at 121° C. for 20 minutes. The crude oil is from the oil reservoir of N 2.

5. Detecting the *Bacillus* in the cultures using molecular biological techniques. A 5 ml of the culture obtained in step 4 was transferred into a sterile centrifuge tube in a sterile condition and centrifuged at 10,000×g for 10 minutes for cell collection, removed the supernatant and added 1 ml distilled water to resuspend the cells sedimentation. DNA in the resuspension were extracted following the manufacturer's protocol of the FastDNA Spin Kit for Soil, and extracted DNA were amplified by PCR using specific 16S RNA gene primers for bacteria to construct clone library, the representative clones was sequenced and determined their phylogenetic affiliations.

Two 16S rRNA gene clone libraries (N2PB and N2IB) were constructed from the two samples following the invention. 6 and 7 OTUs were identified in N2PB and N2IB, respectively. 100% of the sequences in clone library of N2PB and N2IB were identified as *Bacillus*, particularly dominated by *Bacillus halodurans* and *Bacillus* sp. in clone library of N2PB, and dominated by *Bacillus halodurans* in clone library of N2IB (Table 9 and 10).

TABLE 9

Microbes of *Bacillus* detected in the sample of N2-2 by the said method of the invention

| OTU | Clone abundance (%) | The most relative sequences in GenBank | similarity (%) |
|---|---|---|---|
| N2PB-1 | 25.88 | *Bacillus halodurans* AM295065 | 99 |
| N2PB-2 | 63.53 | *Bacillus* sp. AB571604 | 99 |
| N2PB-3 | 7.06 | *Bacillus* sp. AB571604 | 99 |
| N2PB-4 | 1.17 | *Bacillus* sp AB571604 | 99 |
| N2PB-5 | 1.17 | *Bacillus* sp AB571604 | 98 |
| N2PB-6 | 1.17 | *Bacillus* sp. AB571604 | 99 |

TABLE 10 microbes of *Bacillus* detected in the sample of N2-1 by the method of the invention

| OTU | Clone abundance (%) | The most relative sequences in GenBank | similarity (%) |
|---|---|---|---|
| N2IB-1 | 38.4 | *Bacillus halodurans* AB021187 | 99 |
| N2IB-2 | 31.4 | *Bacillus halodurans* AM295065 | 100 |
| N2IB-3 | 25.6 | *Bacillus halodurans* AM295065 | 99 |
| N2IB-4 | 1.2 | *Bacillus halodurans* AM295065 | 99 |
| N2IB-5 | 1.2 | *Bacillus halodurans* HQ184470 | 99 |
| N2IB-6 | 1.2 | *Bacillus* sp. AB571604 | 99 |
| N2IB-7 | 1.2 | *Bacillus* sp. AB571604 | 99 |

A phylogenic tree can be constructed by analysis of the *Bacillus* sequences detected by above-identified 5 examples of the present invention and their most relative homological sequences based on the Basic Local Alignment Search Tool (BLAST) in the GenBank database of the National Center for Biotechnology Information (NCBI) by DNAMMAN software analysis. Wherein, the position of the *Bacillus* detected can be directly presented in the phylogenic tree.

Most of microbes in the samples detected by the methods of the present invention were affiliate with *Bacillus* sp., some of which have low similarities with cultured strains of *Bacillus*, which indicated that most of microbes detected were new species. The present invention can simplify the step of isolation and identification of new strains of *Bacillus* previously considered as uncultivable, which provides a new method for screening potential microbes for MEOR and further provides a research method for ecological study of the *Bacillus* from oil reservoirs.

While the invention has been described in conjunction with the exemplary embodiments described above, it is to be noted that many equivalent modifications and variations will be apparent to those skilled in the art when given in this disclosure. Various changes to the described embodiments may be made without departing from the spirit and the scope of the invention.

The invention claimed is:

1. A quick method for detecting the genus *Bacillus* in samples from oil reservoirs, which comprises:
    (a) collecting a sample from an oil reservoir;
    (b) inactivating microbes through high temperature;
    (c) collecting spores from the inactivated sample;
    (d) incubating the collected spores in an appropriate medium, and stimulating to resurrect the *Bacillus* under the in situ temperature of the oil reservoir; and
    (e) detecting the resurrected *Bacillus* in the cultures using molecular biological techniques,
    wherein said step of inactivating microbes through high temperature comprises transferring 500 ml of the sample into a sterile flask in a sterile condition, sealing the flask with a sterile ventilate membrane, and placing the flask on an electric heater and boiling the sample for 10 minutes, then cooling the sample at room temperature,
    wherein said step of collecting spores from the inactivated sample comprises, after the cooling step, transferring the inactivated sample into 50 ml sterile centrifuge tubes in a sterile condition and centrifuging at 10,000×g for 15 minutes to produce a supernatant and a pellet, transferring the supernatant to a sterile container for medium preparation, resuspending the pellet with 1 ml sterile water, and combining the suspension from all the centrifuge tubes into a 10 ml mixture, the mixture containing spores,
    wherein said medium is compatible with the environment from which the sample was collected, and can provide nutrients for stimulating spores, the medium prepared by solving 2 g molasses, 0.16 g $(NH_4)_2HPO_4$, 0.2 g $KNO_2$ and the supernatant from the collecting step to obtain a 100 ml solution, followed by adding 2 g crude oil from the reservoir from which the sample was collected to the 100 ml solution, and autoclaving at 121° C. for 20 minutes.

2. The quick method for detecting the genus *Bacillus* in samples from oil reservoirs according to claim 1, wherein the method is carried out with samples from various oil reservoirs with different geological conditions and exploitation methods.

3. The quick method for detecting the genus *Bacillus* in samples from oil reservoirs according to claim 2, wherein said samples are selected from samples collected directly from the wellheads of injection wells, oil-water samples collected from production wells, formation water samples, oil-water flowing-back samples of the oil wells, and core samples from oil reservoirs.

4. The quick method for detecting the genus *Bacillus* in samples from oil reservoirs according to claim 3, wherein said step (a) of collecting a sample comprises:

collecting an oil-water sample and placing the sample into sterile plastic bottles, full-filled, sealing the plastic bottles and recording the in situ temperature of the oil reservoir from which the sample was collected.

5. The quick method for detecting the genus *Bacillus* in samples from oil reservoirs according to claim 1, wherein said step (d) of incubating the collected spores in a medium, and stimulating to resurrect the *Bacillus* under the in situ temperature of the oil reservoir comprises:

incubating the 10 ml mixture collected in step (c) in a 100 ml flask with 30 ml sterilized medium, sealing the cover of the flask, cultivating the total 40 ml mixture for 7-15 days at 150 rpm at the in situ temperature of the oil reservoir from which the sample was collected, to resurrect the *Bacillus* and obtain resurrected culture, wherein said in situ temperature of the oil reservoir is from 10° C. to 110° C.

6. The quick method for detecting the genus *Bacillus* in samples from oil reservoirs according to claim 5, wherein said step of detecting the resurrected *Bacillus* in the cultures using molecular biological techniques comprises:

transferring 5 ml of the stimulating medium in the step (d) into a sterile centrifuge tube in a sterile condition, centrifuging at 10,000×g for 10 minutes for cell collection, removing the supernatant and adding 1 ml distilled water to resuspend the pellet;

extracting DNA in the resuspended pellet and amplifying the DNA by PCR using specific 16S RNA gene primers for bacteria to construct a clone library, and sequencing and analyzing the representative clones to determine their phylogenetic affiliations.

\* \* \* \* \*

UNITED STATES PATENT AND TRADEMARK OFFICE
CERTIFICATE OF CORRECTION

PATENT NO. : 9,238,842 B2
APPLICATION NO. : 13/868561
DATED : January 19, 2016
INVENTOR(S) : Fan Zhang et al.

It is certified that error appears in the above-identified patent and that said Letters Patent is hereby corrected as shown below:

In the claims,

Column 12, Line 51, Claim 1, delete "$KNO_2$" and insert -- $KNO_3$ --

Signed and Sealed this
Seventeenth Day of May, 2016

Michelle K. Lee
*Director of the United States Patent and Trademark Office*